(12) United States Patent
Beland et al.

(10) Patent No.: US 7,734,159 B2
(45) Date of Patent: Jun. 8, 2010

(54) DISPERSION DEVICE FOR DISPERSING MULTIPLE VOLATILE MATERIALS

(75) Inventors: Rene Maurice Beland, Waterford, WI (US); Hermann Neumann, Kenosha, WI (US); Jose Porchia, Greenfield, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 951 days.

(21) Appl. No.: 11/513,971

(22) Filed: Aug. 31, 2006

(65) Prior Publication Data

US 2008/0085103 A1 Apr. 10, 2008

(51) Int. Cl.
F24F 6/08 (2006.01)
(52) U.S. Cl. ..................... 392/390; 392/395
(58) Field of Classification Search ......... 392/386–406; 239/34–60; 422/120–125
See application file for complete search history.

(56) References Cited

U.S. PATENT DOCUMENTS

| | | | |
|---|---|---|---|
| 2,686,944 A | 8/1954 | Gubelin | |
| 3,294,005 A * | 12/1966 | Melzer | 454/188 |
| 5,259,062 A | 11/1993 | Pelonis | |
| 5,480,591 A | 1/1996 | Lagneaux et al. | |
| 5,591,409 A | 1/1997 | Watkins | |
| 6,254,065 B1 | 7/2001 | Ehrensperger et al. | |
| 6,390,453 B1 | 5/2002 | Frederickson et al. | |
| 6,443,434 B1 | 9/2002 | Prather | |
| 6,447,731 B1 | 9/2002 | Sun et al. | |
| 6,487,367 B2 | 11/2002 | Vieira | |
| 6,580,875 B2 * | 6/2003 | Rymer | 392/395 |
| 6,581,915 B2 | 6/2003 | Bartsch et al. | |
| 6,619,559 B2 | 9/2003 | Wohrle | |
| 6,713,024 B1 | 3/2004 | Arnell et al. | |
| 6,782,194 B2 | 8/2004 | Schneiderbauer | |
| 6,783,117 B2 | 8/2004 | Wohrle | |
| 6,790,408 B2 | 9/2004 | Whitby et al. | |
| 6,859,615 B2 | 2/2005 | Yip et al. | |
| 6,931,202 B2 | 8/2005 | Pedrotti et al. | |
| 6,950,607 B2 | 9/2005 | Yip et al. | |
| 6,994,328 B2 | 2/2006 | Watkins et al. | |
| 7,011,795 B2 | 3/2006 | Thompson et al. | |
| 7,036,800 B2 | 5/2006 | Ellis | |
| 7,175,815 B2 | 2/2007 | Yamasaki et al. | |
| 7,223,166 B1 | 5/2007 | Wiseman, Sr. et al. | |
| 2002/0088809 A1 * | 7/2002 | Huynh | 220/676 |
| 2004/0028551 A1 | 2/2004 | Kvietok et al. | |

(Continued)

FOREIGN PATENT DOCUMENTS

DE 4033926 10/1991

(Continued)

OTHER PUBLICATIONS

PCT/US2007/019173 International Search Report and Written Opinion dated Jan. 17, 2008.

*Primary Examiner*—Sang Y Paik (57) ABSTRACT

A dispersion device for dispersing volatile materials includes a housing and a plurality of receptacles containing volatile material therein. The device also includes a means for generating or permitting two or more airflows that exit the housing and a switch for adjusting the airflows with respect to speed or path. The plurality of receptacles is connected to the housing such that a portion of the volatile material can be placed into one or more airflows.

11 Claims, 6 Drawing Sheets

U.S. PATENT DOCUMENTS

| | | | |
|---|---|---|---|
| 2004/0033171 A1* | 2/2004 | Kvietok et al. | 422/123 |
| 2004/0101447 A1 | 5/2004 | Tajima et al. | |
| 2004/0131509 A1 | 7/2004 | He et al. | |
| 2005/0001337 A1 | 1/2005 | Pankhurst et al. | |
| 2005/0069307 A1 | 3/2005 | He et al. | |
| 2005/0077376 A1 | 4/2005 | Hess et al. | |
| 2005/0094988 A1 | 5/2005 | Yip et al. | |
| 2005/0147523 A1 | 7/2005 | Laudamiel-Pellet et al. | |
| 2005/0147539 A1 | 7/2005 | Laudamiel-Pellet et al. | |
| 2005/0167860 A1 | 8/2005 | Brooks | |
| 2005/0201944 A1 | 9/2005 | Kvietok et al. | |
| 2005/0205916 A1 | 9/2005 | Conway et al. | |
| 2005/0226788 A1 | 10/2005 | Hrybyk et al. | |
| 2005/0276583 A1 | 12/2005 | Hooks et al. | |
| 2005/0276584 A1 | 12/2005 | Wolf et al. | |
| 2006/0011739 A1 | 1/2006 | Jaworski | |
| 2006/0153731 A1 | 7/2006 | Brown et al. | |
| 2006/0153741 A1 | 7/2006 | Yoshida | |
| 2006/0153744 A1 | 7/2006 | Thompson et al. | |
| 2006/0193611 A1 | 8/2006 | Ballesteros et al. | |
| 2006/0210421 A1 | 9/2006 | Hammond et al. | |
| 2006/0280659 A1 | 12/2006 | Brown et al. | |
| 2006/0288871 A1* | 12/2006 | Crapser et al. | 96/52 |
| 2007/0036688 A1* | 2/2007 | Hayes-Pankhurst et al. | 422/124 |
| 2007/0280653 A1* | 12/2007 | Viera | 392/395 |

FOREIGN PATENT DOCUMENTS

| | | |
|---|---|---|
| GB | 2401047 A | 11/2004 |
| WO | WO 03/028775 | 4/2003 |
| WO | WO 2004/096300 | 11/2004 |
| WO | WO2004093929 A | 11/2004 |
| WO | WO 2005/092400 | 10/2005 |

* cited by examiner

DISPERSION DEVICE FOR DISPERSING MULTIPLE VOLATILE MATERIALS

BACKGROUND OF THE INVENTION

1. Field of the Invention

The present invention relates generally to volatile material dispersion devices, and more particularly to devices for the selective dispersion of multiple volatile materials.

2. Description of the Background of the Invention

Devices for the dispersion of volatile materials, such as, fragrances, odor elimination compounds, and insecticides have utilized aerosol or nebulizer-type devices for such dispersal. Other such devices have alternatively or in addition used one or more heaters and/or a fan to generate an airflow to aid in the dispersion of the volatile.

In one example, a diffusion device includes two heaters for dispersion of fragrances. The device includes a housing, a plug extending from the housing for insertion into an outlet, and two containers having fragrances therein and wicks extending therefrom to absorb fragrances from the containers. Each of the heaters is disposed adjacent one of the wicks to heat the respective wick to vaporize the fragrances therein. Optionally, a CPU controlled by internal software may first activate a first of the two heaters for a predetermined period of time. After the period of time expires, the CPU deactivates the first heater and thereafter activates the second heater.

Other diffusion devices include a housing having a cavity for receiving a cartridge. The cartridge generally has a plurality of scent elements disposed on a rotatable disk. A blower is mounted in the housing to generate an airflow that passes air across a scent element and out an aperture in the housing. The housing further includes rotating means that rotate the rotatable disk, thereby exposing the various scent elements thereon to the airflow. The device diffuses a first scent for a predetermined time period and thereafter rotates the disk to a second scent and diffuses the second scent for the predetermined time period. This process repeats itself until the last scent element is diffused and then the disk is rotated to a home position.

SUMMARY OF THE INVENTION

According to one embodiment, a dispersion device for dispersing a volatile material includes a housing and a plurality of receptacles containing volatile material therein. The device also includes a means for generating two or more airflows that exit the housing and a switch for adjusting the airflows with respect to speed or path. The plurality of receptacles is connected to the housing such that a portion of the volatile material can be placed into one or more airflows.

According to another embodiment, a dispersion device for dispersing multiple volatile materials includes a housing and a plurality of receptacles attached to the housing containing volatile materials, wherein the receptacles have wicks extending therefrom. The device includes a plurality of fans disposed in the housing to generate a plurality of airflows that exit the housing, wherein the wicks extend into the plurality of airflows. A switch associated with each of the plurality of fans controls a parameter of electric power supplied to the fan to control its speed.

According to yet another embodiment, a method for dispersing two or more volatile materials includes the step of generating two or more airflows and selectively controlling the respective airflows with respect to rate or path of flow. The method further includes the step of placing the volatile materials into the airflows.

Other aspects and advantages of the present invention will become apparent upon consideration of the following detailed description.

DETAILED DESCRIPTION OF THE PREFERRED EMBODIMENTS

Dispersion devices of the present invention preferably include a housing and a plurality of receptacles disposed internally or externally with respect to the housing so long as the contents of the receptacles may be placed into airflows that exit from the housing. Suitable receptacles are available in a wide variety of formulations from S. C. Johnson & Son, Inc., of Racine, Wis., under the GLADE® PLUGINS®, OFF® and RAID® brand names, for example. Preferably, the receptacles are disposed in a cavity of the device. More preferably, additional receptacles are included with the present invention. The additional receptacles can be attached to the inside or the outside of the housing, or to both the inside and the outside thereof, or provided separate from the housing as separate individual receptacles or sets thereof. The individual receptacles or sets thereof are preferably packaged, such as in a free-standing rack or a box. Even more preferably, the additional receptacles are configured and/or packaged to be free-standing or attached to the housing or capable of either. Additionally, the device may include multiple removably attached modules, wherein each module is an independent dispersion device that contains one or more receptacles and that has a means of generating one or more airflows that disperse the contents of the receptacles.

Still further, the housing may include an attachment member in the form of an outwardly extending member or structures defining one or more apertures, to which a complementary structure on a given receptacle allows attachment of the receptacle to the housing. The attachment member on the housing can be on the inside or on the outside of the housing.

The receptacles are preferably easily removable from the housing. The attachment member can have any suitable form that forms either a complementary fit or other securement, such as, for example, a clamp, a snap, structures defining an interference fit, a threaded screw attachment, suitable adhesives, and the like. In yet other embodiments, the receptacles are securely and non-removably fixed to the housing. In these embodiments, it is preferred that the receptacles are refillable, wherein the refill materials therefor are the same or different as the original content of the respective receptacles. Alternatively, the present invention includes both fixed and removable receptacles.

The receptacles preferably contain wholly or partially volatile materials. Preferred materials, in addition to having suitable volatility characteristics as set forth herein, also have user-impacting characteristics that relate to odor, mood, drug delivery, insecticidal characteristics, insect repellants, and the like. With respect to odor, the volatile materials can (a) introduce a fragrance to an area, or (b) reduce or eliminate an existing odor in an area. Preferred volatile materials include the following without limitation: perfumes, scented oils, liquids, or gels, aromatherapy substances, air fresheners, or insecticides. Particular volatiles may include, without limitation, any one or more of the following chemicals: esters, aldehydes, alcohols, aromatic organic compounds, oxygen- or enzyme-based deodorizers, insect control compositions including transfluthrin, tefluthrin, and vaporthrin, or the like. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Orange, Origanum, Petitgrain, White Cedar, Patchouli, Lavandin, Neroli, Rose absolute, and the like.

The materials within the receptacles need not be wholly volatile, and some of the materials may be non-volatile; nonetheless, as used herein, the term "volatile material" refers to the material included in the receptacles that are used in the context of the present invention. The material in a receptacle may, in one embodiment, include a substantially non-volatile material to stabilize the volatile material. Examples of stabilizing materials include, without limitation, an inert matrix or gel.

By the term "substantially volatile," as used in the context of the present invention, it is intended that one having unimpaired olfactory and nervous tissue or other sensory nervous system capability, as appropriate, will sense or experience the effect of at least the volatile material included in the receptacles when the contained material is preferably placed in an airflow at ambient room temperature and pressure. Preferably, ambient room temperature and pressure is between about 22° and 28° Celsius at sea level; higher temperatures or elevation will generally increase the volatility of the contained materials and lesser temperatures or elevation will reduce the volatility thereof. Conversely, the term "substantially non-volatile" as used herein also refers to a material that is not readily detected in the atmosphere at ambient room temperature and pressure, even when the material is heated in heat-included embodiments of the present invention.

Preferably, the volatile materials used in the context of the present invention will be sensed upon exposure thereof to an airflow at ambient room temperature at any elevation where humans reside or domestic animals are kept. However, more preferably, the volatile materials used have dispersal characteristics that are designed for optimal use at or near sea level. In an alternative embodiment, the volatile materials employed have dispersal characteristics that are designed for optimal use in submersible or aviation vessels. Yet another alternative embodiment includes volatile materials that have dispersal characteristics that are designed for optimal use at higher elevations, such as above about 1000 m elevation, for example. Such materials preferably have lesser volatility relative to materials employed at sea level or below. Therefore, a user's ability to customize the dispersion of volatile materials in such varying conditions will depend, in part, on varying the materials employed, as noted above, and/or allowing a user to adjust the intensity of the dispersion using controllable fans and/or heating elements, for example.

In order to effectively disperse the volatile material, it needs to be exposed to the airflow. Exposure after manipulating the material so that its surface area is increased is preferred. For example, the material can be aerosolized or atomized (i.e., formed into small particles thereof) using well-known principles and instruments, such as a nebulizer or a piezoelectric liquid atomizer. In one embodiment, accordingly, the volatile material is formed into small particles, placed into the airflow, and allowed to exit the housing of the present invention as an aerosol. In another embodiment, the volatile material, whether in the form of a liquid or an aerosol, evaporates into the atmosphere. In yet another embodiment, the degree of volatility of the material contained in the receptacles is adjusted via agents known to impact such characteristics. Any given material usefully dispersed via the present invention will have a known or knowable degree of volatility. One skilled in the relevant art would use the degree of volatility to configure the present invention to increase aerosolization of materials of lower volatility, and vice versa; i.e., evaporation will be allowed from the liquid or gel form of a material that has a higher level of volatility, whereas evaporation will be facilitated in material that has a lower level of volatility by aerosolizing same. Additionally, a heating element may be used to heat the volatile material and increase its volatility in that manner. These considerations are well-understood in the art, as are methods of determination of volatility, concentration for appropriate effect of the material, and implementation of the various noted methods.

Preferably a fluid conduit is used in order to increase the rate of bringing the volatile material into the path of the airflow in contrast to not using a fluid conduit wherein the volatile material goes directly from the receptacle into the airflow. A fluid conduit is any structure that serves to reposition the volatile material from the receptacle to the airflow. Examples of fluid conduits include, without limitation, (a) hollow channeled structures, such as a tube, (b) compartmented structures, such as a metallic or ceramic structure composed of a series of concavities or cavities that are able to be in fluid communication with one another, and (c) absorbent structures. More particularly, fluid conduit is composed of a solid, preferably flexible, more preferably absorbent material.

A preferred fluid conduit is a wick, i.e., a bundle of fibers or a loosely twisted, braided, or woven cord, tape, or tube that is composed of natural or synthetic fibers. As further described below, the series of compartments capable of fluid communication therebetween or the wick can comprise organic or inorganic matter, so long as the structure is able to facilitate movement of the volatile material by capillary action.

When employed, the wick is placed in contact with the volatile material in the receptacle directly or indirectly. Indirect contact can be effected by use of a second fluid conduit that provides a path for the volatile material to flow from the receptacle to a position that is proximate to the airflow, as further described below. Either way, the wick is preferably in contact with the volatile material at the wick's proximate end relative to the receptacle. The wick's distal, exposed end extends from the source of the volatile material and is disposed in one or more airflows. This configuration results in delivering the volatile material from the receptacle to the wick, then from the wick into the airflow within the housing, and then, as the airflow exits the housing, into the environment.

In the embodiment where the wick has indirect contact with the receptacle, a second fluid conduit is used to deliver the volatile material from the receptacle to the wick. For example, a plastic tube may be used to deliver the volatile material from a receptacle to the wick, wherein the receptacle may be contained internally or externally to the housing. Alternatively, the tube may deliver the volatile material to a secondary receptacle or holding tank for delivery to the wick. The volatile material may then enter the airflow as described above.

Preferred wick materials include, without limitation, fibrous cloths, whether synthetic or natural fiber, or porous ceramics, plastics, or metals. Generally, the receptacle and wick arrangement will be made available to users in combination with an additional cap or other covering to protect the wick during transportation and storage and to prevent the evaporation or dispersion of the volatile material until desired.

Figure 1:
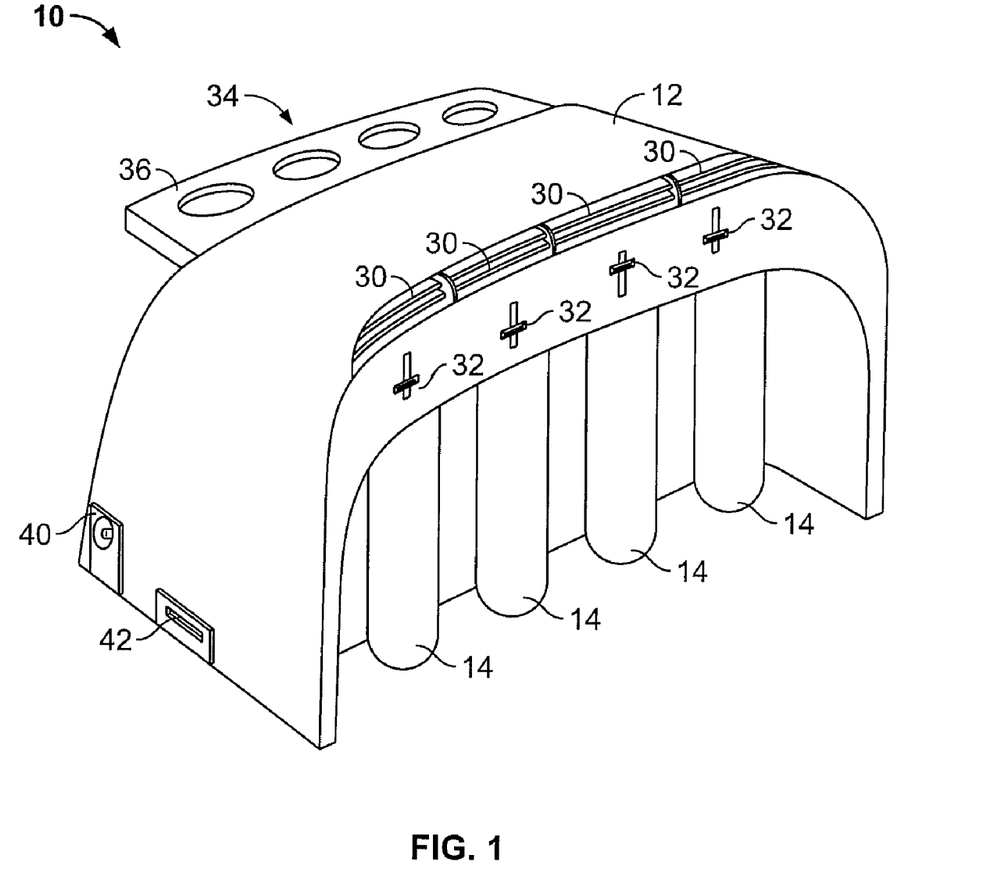
FIG. 1 is a perspective view showing a diffusion device with receptacles disposed within the housing according to one embodiment of the present invention.
Figure 2:
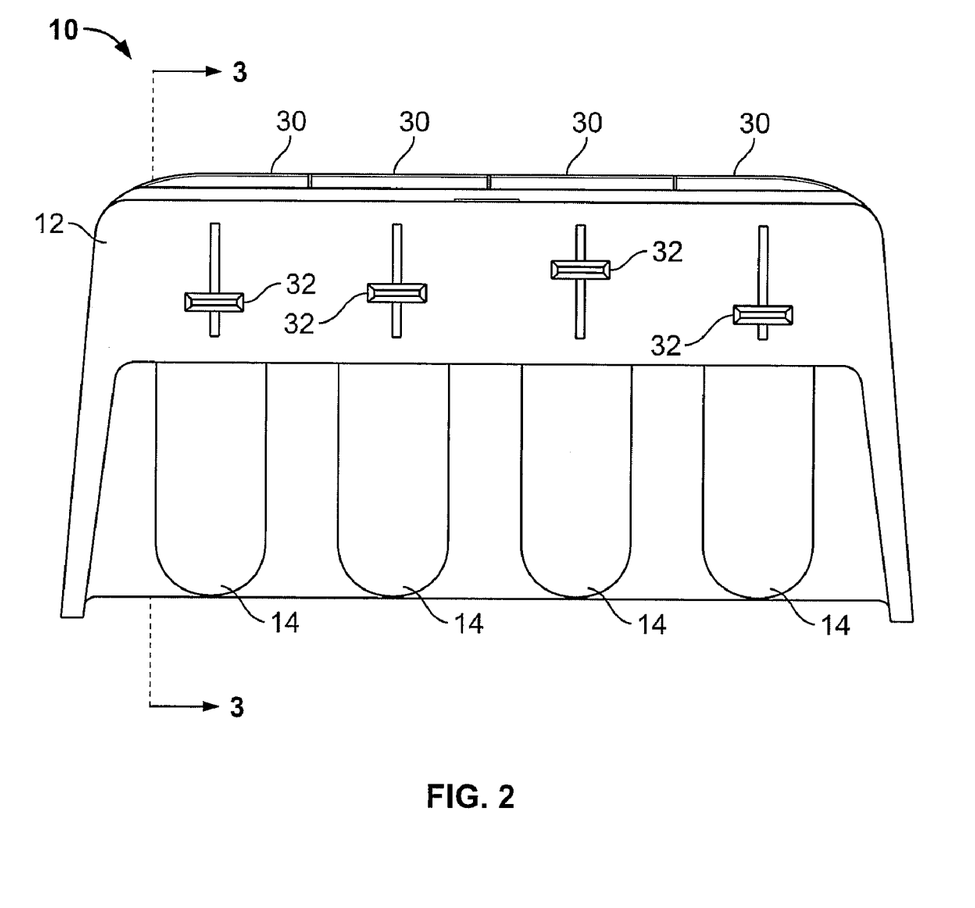
FIG. 2 is a front elevational view of a diffusion device of the embodiment of FIG. 1.
Figure 3:
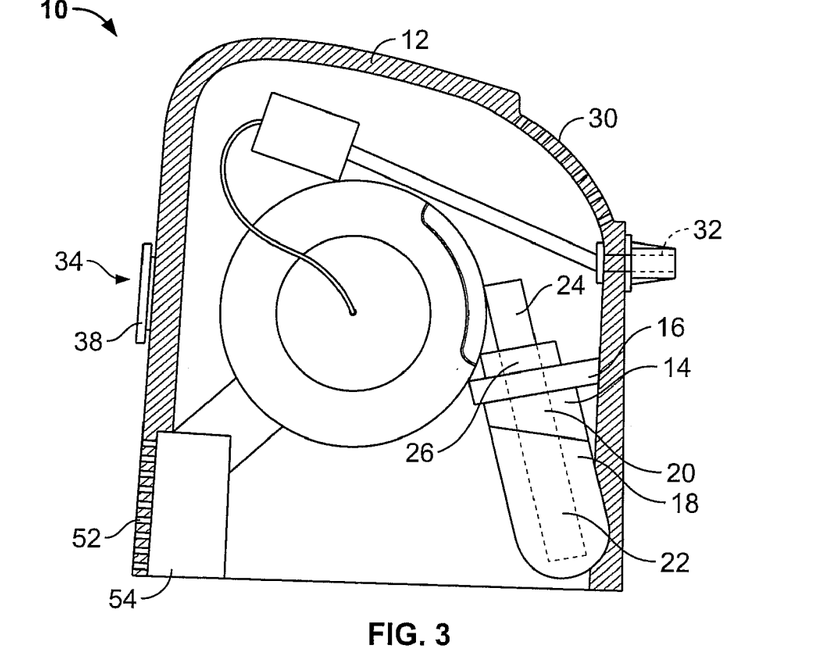
FIG. 3 is a sectional view taken generally along lines 3-3 of FIG. 2 with portions behind the section plane omitted for clarity.
Figure 4:
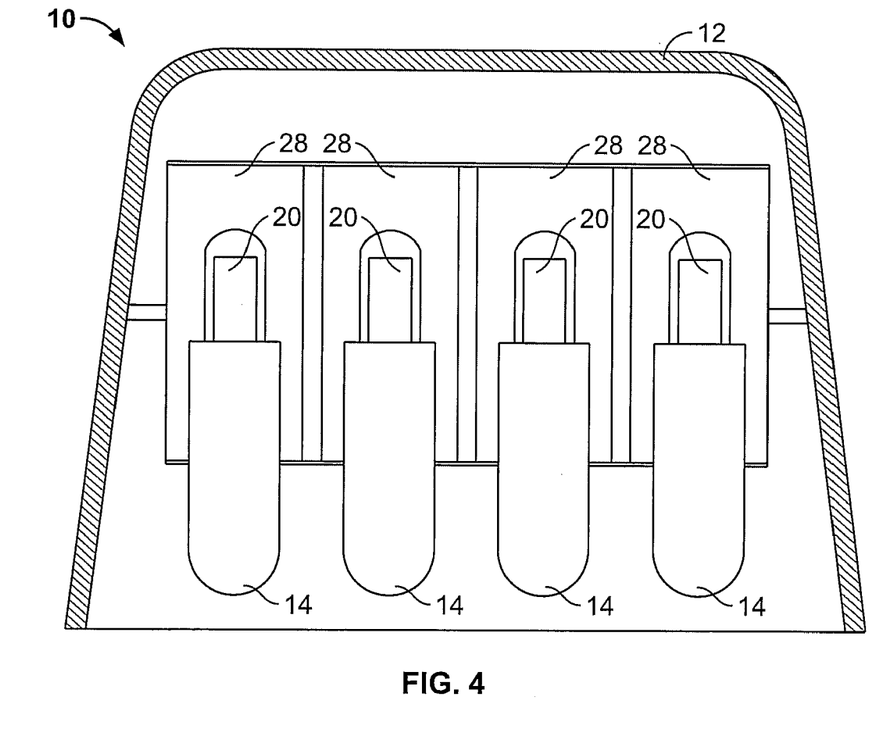
FIG. 4 is a front view of the embodiment of FIGS. 1-3, showing the upper portion of the device housing partially cut away.

In one embodiment, the device preferably includes a plurality of fans or pumps positioned to create an airflow that passes through the exposed distal portions of the wicks to aid in the evaporation and dispersal of the volatile material. The fans or pumps can be of any type appropriate to generate an airflow, including, for example, an axial propeller-type fan, a centrifugal-type squirrel cage blower, or a peristaltic pump. Preferably, the device includes a plurality of fans. The fans shown in FIGS. 3 and 4, as one example, are variable speed centrifugal-type fans where the airflow direction is radial to the shaft of the fan blade. The receptacles are preferably disposed in the housing so that the wicks are exposed to the airflow generated by the plurality of fans, wherein the airflows blow through the wicks and exit the device through a plurality of vents aligned with the plurality of receptacles. If desired, the vents may be adjustably positioned in a louvered manner. Each fan is preferably disposed to create an airflow that is primarily directed at a corresponding one of the wicks. Each fan is preferably wired to be turned on or off and adjusted independently. More preferably, the speed of the fans is independently controlled. Accordingly, an individual can select the desired volatile material to be dispersed and the intensity or rate of the dispersion. The fans can be controlled by adjusting a parameter of electric power supplied to same, such as, voltage or current, increasing the parameter supplied to increase speed and lowering the parameter to decrease speed or turn off the fan. The power to the fans may be continuous or intermittent. An example of the latter is operation in a pulse-width mode of operation. There is a switch associated with each fan for the control thereof, which includes either a single switch to control multiple fans or multiple switches for controlling multiple fans.

In another embodiment, one or more fans may be adjusted to generate a reverse airflow that sucks air into the housing through the vents that then passes about the wicks or through an air filter attachment. Preferably, the fans are each adjustable to generate airflows that exit or enter the device, wherein the housing has appropriate attachment means for attaching various types of receptacles and filters. More preferably, the housing includes in-flow and out-flow vents, wherein the fans are configured to generate an airflow that enters the housing through an in-flow vent, which is then passed through one or more air filters. The filtered air is then passed through a wick saturated with a volatile material as the airflow exits the housing through one or more out-flow vents. The size, arrangement, and number of in-flow and out-flow vents can be adjusted to provide an adequate airflow through the one or more air filters and wicks. This configuration allows a user to both circulate and filter the air in the environment and also disperse volatile materials, such as fragrances, using a single multipurpose device.

In another embodiment, the plurality of airflows is generated by a combination of at least one fan, one or more air conduits, and one or more baffles by which a single airflow from a fan can be divided into multiple airflows that are associated with multiple receptacles or wicks, respectively. The airflow is permitted to flow through different air paths defined by the baffles or air conduits, such as by rotating a fan to direct the airflow to the different paths or by opening and closing vents or baffles while keeping the fan stationary so that the airflow is selectively divided. Accordingly, a separate control may be used to indirectly control the direction of the airflow, such as by opening and closing vents or baffles, instead of directly controlling the power supplied to the fan. Preferably, a single control could be used to control both the power supplied to the fan and the direction of the airflow.

In addition, the device can be powered by any appropriate power supply for supplying electric power to the device for operation of the fans and any other component requiring electric power herein described explicitly or implicitly. For example, batteries or solar energy or house current (by plugging the device into a standard wall outlet) can provide the necessary power supply. Preferably, the device is powered by batteries and/or a power input for plugging the device into a standard wall outlet. More preferably, the device is capable of receiving electric power at 120V or 240V.

The device may also include a communication port for communicating with the switch(es) that allows a user to selectively control the dispersion of the multiple volatiles remotely via a wireless signal or a cable-type connection. More preferably, the communication port develops or is responsive to a wireless signal, wherein a user may control the device via a computer over wireless internet, a wireless remote control, or the like.

In addition, the housing preferably includes a holder for holding additional refill or display receptacles. In one embodiment, the holder is an attached plate with appropriately sized openings, wherein the receptacles are seated. More preferably, the holder includes an engagement structure on the housing that engages the caps of the receptacles or some other portion of the receptacles. A more preferred holder is a structure that is substantially flush with the housing to minimize the size of the device in consideration of packaging and user preferences. Other types of holders may be removably attached to the housing, for example, a package of refill receptacles available to consumers can be removably attached to the housing with a clip or magnet or other suitable form of attachment.

Those skilled in the mechanical arts can readily take the embodiments of the present invention set forth herein and produce them using available technology and parts. In order to provide further description of a number of embodiments, a series of figures are provided herein along with the following description. These figures are intended to be illustrative of the embodiments shown thereby and are not intended to be limitative of the scope of the present invention.

Referring now more particularly to the embodiment of the present invention shown in FIGS. 1-4, the device 10 includes a housing 12 and a plurality of receptacles 14, wherein each receptacle is disposed in the housing via an attachment member 16 and each receptacle contains a volatile material 18 and a wick 20. A first or proximal end 22 of each wick 20 is in contact with the volatile material 18 contained in the receptacles 14 and a second or distal end 24 of each wick opposite the first or proximal end extends beyond an upper portion 26 of the receptacles. The housing includes a plurality of fans, such as squirrel cage-type fans 28, wherein each receptacle 14 is associated with a fan and each wick 20 is placed in the path of an airflow generated by each fan as it exits the housing 12 through one ore more vents 30. Additionally, the housing 12 may include one or more vents 52 through which the fan 28 draws the airflow into the housing and passes it through an air filter attachment 54. The filtered air is then passed through the wick 20 as it exits the housing 12 through vents 30.

A plurality of switches 32 are disposed on the housing 12 for controlling the correspondingly positioned fans 28 by turning them on or off and adjusting the speed and/or direction of the fans while on. Multiple fans 28 may be turned on at the same time and the respective speeds thereof adjusted independently so that a user may selectively disperse a single volatile material 18 or multiple volatile materials and also adjust the intensity of the dispersion. A holder 34 is included in the form of a plate 36 or engagement structure 38 for holding additional or refill receptacles. Additionally, the housing 12 includes a power input 40 for receiving power from a standard wall outlet. A communication port 42 is also disposed on the housing 12 for allowing a user to remotely control the device 10. The communication port 42 may be responsive to a wireless signal, for example via wireless internet or a cellular signal, or may include a cable connection to a computer or other remote device.

Figure 5A:
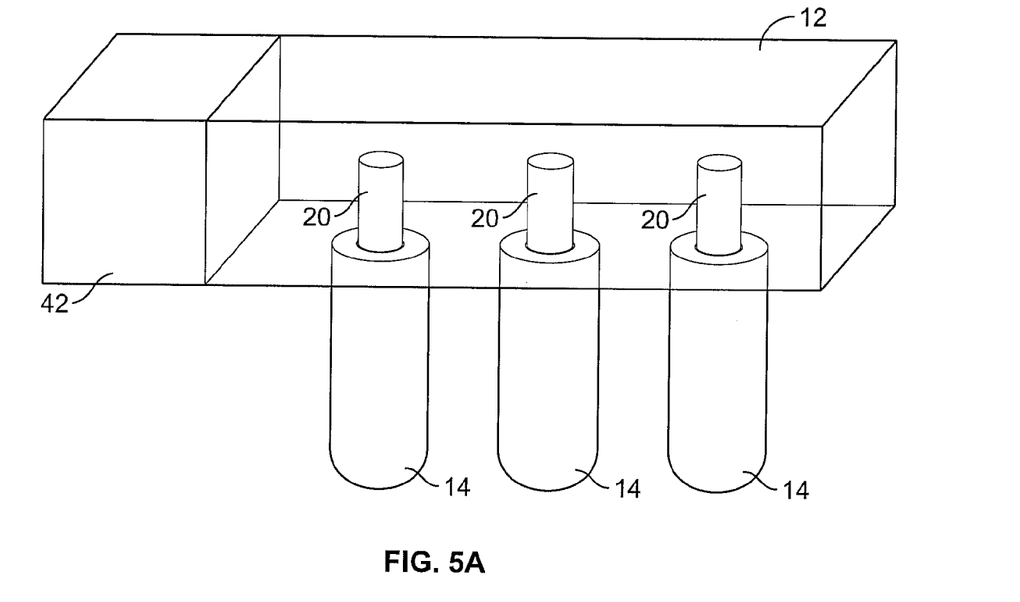
FIG. 5A is a diagrammatic isometric view of another embodiment of the invention.
Figure 5B:
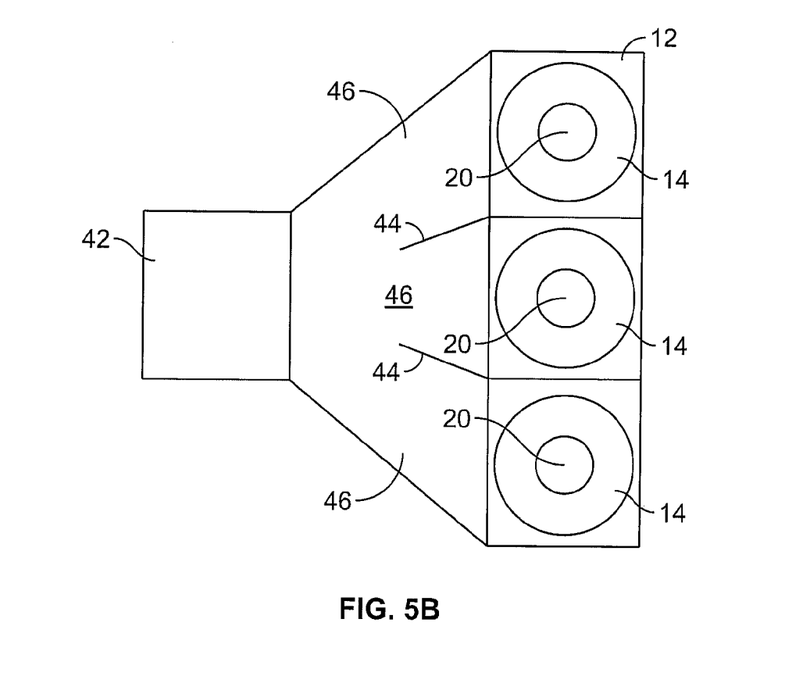
FIG. 5B is a top diagrammatic view of a yet another embodiment of the invention.

FIGS. 5A and 5B show further embodiments of the present invention with housing 12 where a single airflow is passed through multiple wicks 20 extending from receptacles 14 containing volatile material therein. The airflow can be generated by any appropriate device, for example, an axial propeller fan, a squirrel cage blower, or a peristaltic pump. In FIG. 5A, housing 12 includes an axial propeller fan 42 that is used to generate a single airflow and multiple receptacles 14 are arranged directly in-line with the airflow as it exits the housing 12. FIG. 5B shows another embodiment where a single fan 42 generates an airflow that is divided as it exits the housing 12 via multiple baffles 44 defining separate air conduits 46. Preferably, a single receptacle is associated with each air conduit; however, in other embodiments, multiple receptacles and/or wicks may be associated with each air conduit.

Figure 6A:
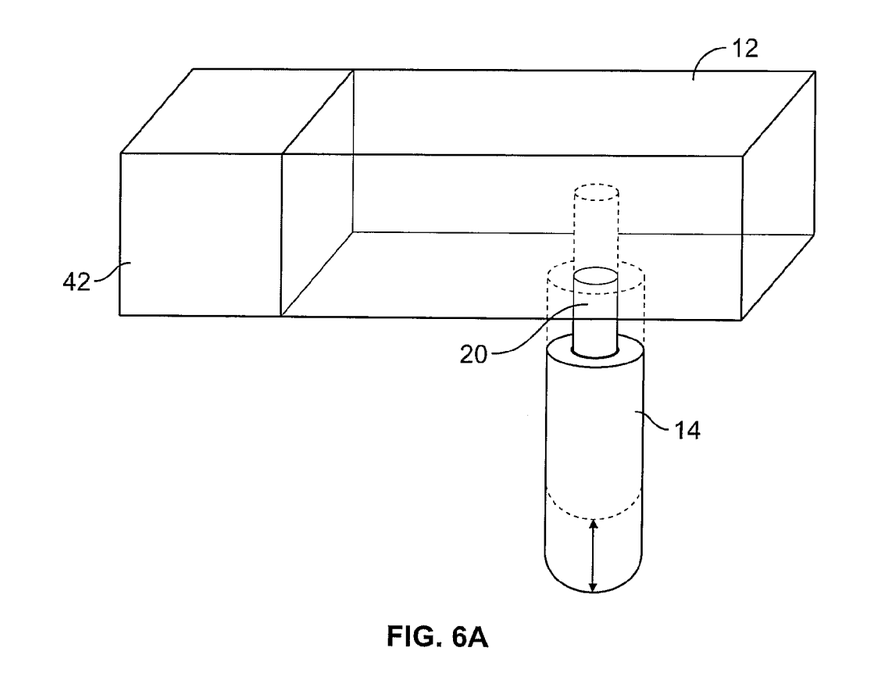
FIG. 6A is a diagrammatic isometric view of a further embodiment of the invention.
Figure 6B:
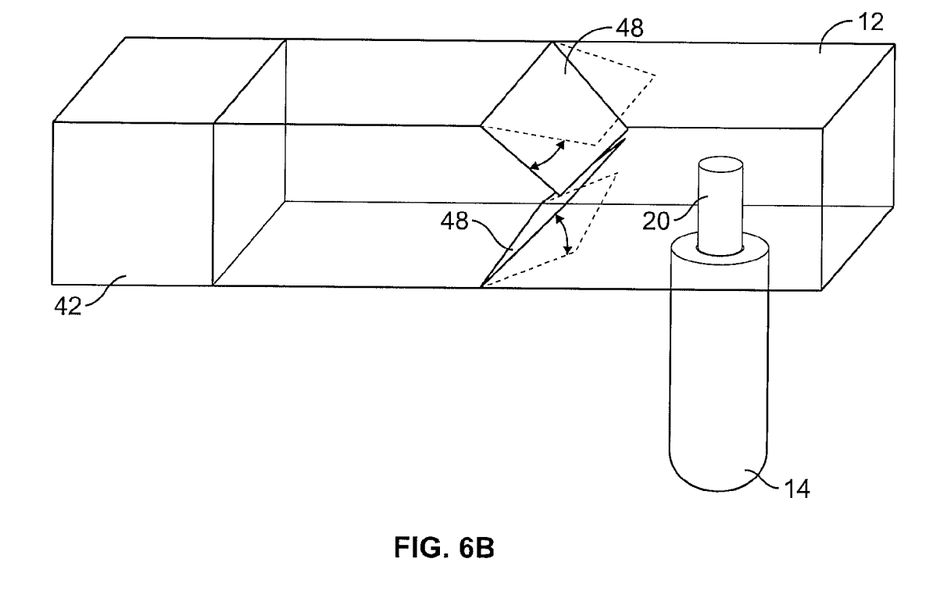
FIG. 6B is a diagrammatic isometric view of an embodiment of the invention including adjustable panels.
Figure 7A:
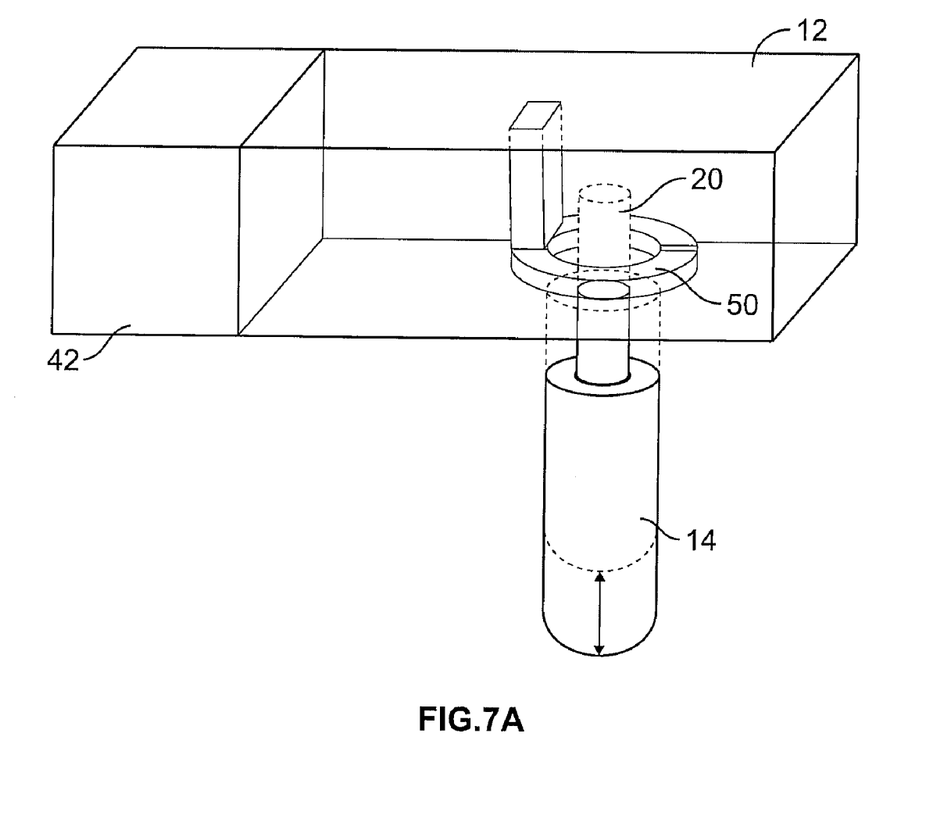
FIG. 7A is a diagrammatic isometric view of an embodiment of the invention including a heating element.
Figure 7B:
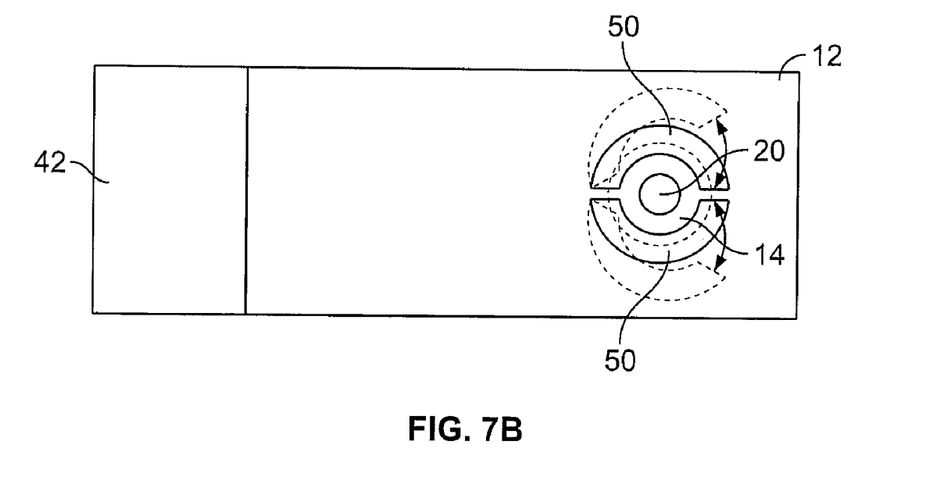
FIG. 7B is a top diagrammatic view of another embodiment of the invention including a heating element.

FIGS. 6A, 6B, 7A, and 7B show various embodiments that allow a user to selectively control the dispersion of volatile materials contained in multiple receptacles. FIGS. 6A and 6B illustrate embodiments where the dispersion is adjusted by increasing or decreasing the surface area of the wick exposed to the airflow. FIGS. 7A and 7B illustrate embodiments where one or more heating elements are used to adjust dispersion. Each of the embodiments in FIGS. 6A-7B may be adapted for use, either singly or in combination, with the embodiments of FIGS. 1-5B or any other suitable arrangement that allows the contents of receptacles containing volatile material to be placed into one or more controllable airflows.

In one embodiment shown in FIG. 6A, the housing 12 includes a fan 42 that generates an airflow that passes over a wick 20 extending from receptacle 14 containing volatile material. The wick 20 and/or the receptacle 14 are moved with respect to the airflow to adjust the dispersion of the volatile material. The wick and/or receptacle may be moved by any appropriate means, for example, a ratcheting or gear mechanism, the details of which are not necessary to a full understanding of the present invention. To increase intensity of the dispersion, the receptacle 14 and wick 20 are moved into the airflow (shown in dotted lines) to expose a larger surface area of the wick to the airflow. Alternatively, the receptacle 14 and wick 20 are moved out of the airflow to expose a smaller surface area of the wick to the airflow, thereby decreasing the intensity of the dispersion. The receptacle 14 and wick 20 may be moved so that the wick is completely out of the direct path of the airflow to decrease dispersion to a substantially unnoticeable amount and to minimize waste of the volatile material until the user once again desires to disperse the volatile. FIG. 6A illustrates the movement of a single receptacle and wick into and out of the airflow; however, preferably, multiple receptacles are used, for example, as in FIGS. 1-5B, wherein the positions of each receptacle or wick are adjusted with respect to one or more airflows.

FIG. 6B illustrates another embodiment of the present invention, wherein the housing 12 includes adjustable panels 48 that control the size of the air path through which an airflow generated by a fan 42 travels as it passes through the wick 20 and exits the housing. This present embodiment utilizes two panels 48 that can be moved closer together to decrease the size of the air path and moved farther apart to increase the size of the air path (shown in dotted lines). A smaller air path will generally decrease the dispersion of the volatile material by decreasing the surface area of the wick 20 exposed to the direct path of the airflow. Alternatively, a larger air path will increase the dispersion of the volatile by increasing the surface area of wick 20 exposed to the airflow. Preferably, the use of adjustable panels 48 will be implemented with the use of multiple airflows and multiple receptacles as in the embodiments of FIGS. 1-4 or FIG. 5B, for example. Additionally, the adjustable panels 48 may be used with moveable wicks 20, as in the embodiment of FIG. 6A, to further control the dispersion of the volatile material.

In further embodiments, the dispersion device includes one or more heating elements for heating the volatile material to customize dispersion. In FIGS. 7A and 7B, a heating element 50 is preferably positioned to apply heat to the wick 20 to adjust dispersion of the volatile material as an airflow generated by a fan 42 passes through the wick and exits the housing 12. The heating element 50 is preferably a toroidal shaped element with electrical-resistance properties; however, the heating element can be of any suitable shape and type for heat generation, for example, a flat plate or an elongate pillar element of a printed electric-conductive ink or electric-conductive polymer. In FIG. 7A, the receptacle 14 and the wick 20 are moved with respect to the heating element 50 to increase dispersion by heating a greater surface area of the wick (shown in dotted lines) or to decrease dispersion by heating a lesser surface area of the wick. The mechanism for moving the receptacle and wick may be the same as, or different than, the mechanism used in the embodiment of FIG. 6A. However, similar to FIG. 6A, the movement of the receptacle 14 and wick 20 generally changes the surface area of the wick exposed to the airflow. In FIG. 7B, the heating element 50 is adjusted to be moved closer to the wick 20 to apply more heat to the wick and increase dispersion and moved away from the wick (shown in dotted lines) to apply less heat to the wick and decrease dispersion. Preferably, the intensity and duration of the heat applied by the heating element 50 is also controllable to further allow a user to customize dispersion. The use of heating elements is preferably used with multiple receptacles, as in any of the previously described embodiments.

INDUSTRIAL APPLICABILITY

The embodiments disclosed herein are operable to provide a selective dispersion of multiple volatile materials. Multiple airflows are used to selectively disperse the desired volatile material and the airflows are controllable as to speed and path to control the intensity and selection of the desired volatile.

Numerous modifications to the present invention will be apparent to those skilled in the art in view of the foregoing description. Accordingly, this description is to be construed as illustrative only and is presented for the purpose of enabling those skilled in the art to make and use the invention, as well as to teach the best mode of carrying out same. The exclusive rights to all modifications that come within the scope of the appended claims are reserved.

We claim:

1. A dispersion device for dispersing a volatile material, comprising:
    a housing;
    a plurality of receptacles each containing a volatile material therein and wicks in contact with the volatile materials and extending from the receptacles;
    means for generating two or more airflows that exit the housing;
    a switch for adjusting the airflows with respect to speed or path,
    wherein the plurality of receptacles is connected to the housing such that a portion of each of the volatile material can be placed into one or more airflows; and
    at least one toroidal shaped heating element surrounding at least one of the wicks, the toroidal shaped heating element being adjustable to move closer or farther away from the at least one of the wicks, wherein the heating element is adjustable along a horizontal plane.

2. The dispersion device of claim 1, wherein the airflow generating means is selected from the group consisting of fans, pumps, blowers, and air conduits and baffles therefor.

3. The dispersion device of claim 2, wherein one or more switches are employed for controlling a parameter of electric power supplied to the airflow generating-or-permitting means.

4. The dispersion device of claim 3, wherein the switch or switches indirectly control the airflow.

5. The dispersion device of claim 1, further comprising a panel that is connected to the housing, wherein the airflow is permitted or blocked by opening or closing the panel.

6. The dispersion device of claim 1, further comprising at least one air filter that is disposed to intercept air that enters the housing.

7. The dispersion device of claim 1, wherein the housing includes a plurality of vents that align with the wicks and are configured to control the direction of airflow exiting the housing.

8. The dispersion device of claim 1, wherein the wicks and respective airflows are moveable with respect to each other.

9. The dispersion device of claim 1, further comprising a plurality of heating elements that are disposed proximate to each volatile material such that each volatile material is heated.

10. The dispersion device of claim 1, wherein the housing includes a holder for additional or refill receptacles.

11. The dispersion device of claim 1, wherein the housing includes a communication port for communicating with the switch.

* * * * *